US012766096B2

(12) United States Patent
Graham et al.

(10) Patent No.: US 12,766,096 B2
(45) Date of Patent: Oct. 20, 2026

(54) HIGH CONCENTRATION PHARMACEUTICAL COMPOSITIONS OF ROFLUMILAST FOR OPHTHALMIC DELIVERY

(71) Applicant: Iolyx Therapeutics, Inc., Burlingame, CA (US)

(72) Inventors: Richard Graham, Irvine, CA (US); Elizabeth W. Jeffords, Hillsborough, CA (US); Hovhannes J. Gukasyan, Orange, CA (US); Shannon Dahl, Palo Alto, CA (US)

(73) Assignee: IOLYX THERAPEUTICS, INC., Burlingame, CA (US)

( * ) Notice: Subject to any disclaimer, the term of this patent is extended or adjusted under 35 U.S.C. 154(b) by 266 days.

(21) Appl. No.: 18/368,832

(22) Filed: Sep. 15, 2023

(65) Prior Publication Data

US 2024/0115491 A1 Apr. 11, 2024

Related U.S. Application Data

(60) Provisional application No. 63/407,366, filed on Sep. 16, 2022.

(51) Int. Cl.

| | |
|---|---|
| ***A61K 9/00*** | (2006.01) |
| ***A61K 31/44*** | (2006.01) |
| ***A61K 47/02*** | (2006.01) |
| ***A61K 47/12*** | (2006.01) |
| ***A61K 47/26*** | (2006.01) |
| ***A61K 47/38*** | (2006.01) |

(52) U.S. Cl.

CPC .......... *A61K 9/0048* (2013.01); *A61K 9/0019* (2013.01); *A61K 31/44* (2013.01); *A61K 47/02* (2013.01); *A61K 47/12* (2013.01); *A61K 47/26* (2013.01); *A61K 47/38* (2013.01)

(58) Field of Classification Search

CPC ........ A61K 31/44; A61K 47/02; A61K 47/12; A61K 47/26; A61K 47/38

See application file for complete search history.

(56) References Cited

U.S. PATENT DOCUMENTS

| | | | |
|---|---|---|---|
| 5,712,298 | A | 1/1998 | Amschler |
| 6,872,382 | B1 | 3/2005 | Gamache et al. |
| 7,576,069 | B2 | 8/2009 | Rieger et al. |
| 7,605,143 | B2 | 10/2009 | Rieger et al. |
| 8,497,379 | B2 | 7/2013 | Choi-Sledeski et al. |
| 8,614,210 | B2 | 12/2013 | Bhutada et al. |
| 8,663,694 | B2 | 3/2014 | Bruck-Scheffler et al. |
| 9,115,133 | B2 | 8/2015 | Barawkar et al. |
| 9,192,623 | B2 | 11/2015 | Scott |
| 12,102,622 | B2 | 10/2024 | Chaudhuri et al. |
| 2002/0035264 | A1 | 3/2002 | Kararl et al. |
| 2006/0084684 | A1 | 4/2006 | Bolle et al. |
| 2006/0084685 | A1 | 4/2006 | Koenen et al. |
| 2006/0257486 | A1 | 11/2006 | Owen et al. |
| 2007/0203209 | A1 | 8/2007 | Bartolini et al. |
| 2007/0259009 | A1 | 11/2007 | Linder |
| 2008/0255209 | A1 | 10/2008 | Klein et al. |
| 2009/0186923 | A1 | 7/2009 | Armer et al. |
| 2009/0209599 | A1 | 8/2009 | Endo et al. |
| 2011/0086023 | A1 | 4/2011 | Lane |
| 2012/0283252 | A1* | 11/2012 | Bhutada .................. A61P 27/02 514/226.5 |
| 2014/0155381 | A1 | 6/2014 | Baloglu et al. |
| 2015/0125539 | A1 | 5/2015 | Popov et al. |
| 2015/0272936 | A1 | 10/2015 | Vakkalanka et al. |
| 2015/0366890 | A1 | 12/2015 | Collins et al. |
| 2016/0045508 | A1 | 2/2016 | Vazquez et al. |
| 2019/0192691 | A1 | 6/2019 | Barrett et al. |
| 2020/0129461 | A1 | 4/2020 | Bannister et al. |
| 2021/0244718 | A1 | 8/2021 | Osborne |
| 2021/0346661 | A1 | 11/2021 | Johnson et al. |
| 2022/0249451 | A1 | 8/2022 | Chaudhuri et al. |

(Continued)

FOREIGN PATENT DOCUMENTS

| | | | |
|---|---|---|---|
| EP | 1796668 | B1 | 9/2008 |
| EP | 1906916 | B1 | 10/2008 |

(Continued)

OTHER PUBLICATIONS

Asasutjarit et al. ( Gamma sterilization of diclofenac sodium loaded-N-trimethyl chitosan nanoparticles for ophthalmic use), Carbohydrate Polymers, 157 (2017) 603-612.*

International Search Report and the Written Opinion of the International Searching Authority, issued in corresponding International Application No. PCT/US2022/076726, dated Nov. 25, 2022, 20 pages.

International Search Report and the Written Opinion of the International Searching Authority, issued in corresponding International Application No. PCT/US2022/076826, dated Dec. 15, 2022, 17 pages.

Sakkas et al., “Phosphodiesterase 4 Inhibitors in Immune-mediated Diseases: Mode of Action, Clinical Applications, Current and Future Perspectives,” Current Medicinal Chemistry (2017), 24, 3054-3067.

Tan et al., “Analysis of Th17-associated cytokines in tears of patients with dry eye syndrome,” Eye (2014), 28, 608-613.

(Continued)

*Primary Examiner* — Zohreh A Fay

(74) *Attorney, Agent, or Firm* — Rothwell, Figg, Ernst & Manbeck, P.C.

(57) ABSTRACT

The present invention relates to high concentration ophthalmic pharmaceutical formulations of the phosphodiesterase-4 inhibitor, roflumilast, which are suitable for intravitreal or other ocular administration to injection sites internal or external to the eye and orbit. The compositions can comprise about 2% to about 5% w/v of roflumilast, a viscosity agent, a tonicity agent, a buffer agent, a surfactant, and water. The pharmaceutical compositions are stable with little to no impurities and can be injected from a 27 Gauge or 30 Gauge syringe with minimal force, resulting in therapeutic levels of pharmaceutical in relevant tissues for the ocular surface, anterior compartment, vitreous/posterior compartments, and tissues or chambers surrounding the eye.

19 Claims, 8 Drawing Sheets

(56) References Cited

U.S. PATENT DOCUMENTS

| | | | |
|---|---|---|---|
| 2023/0088371 | A1 | 3/2023 | Graham et al. |
| 2023/0090417 | A1 | 3/2023 | Jeffords et al. |

FOREIGN PATENT DOCUMENTS

| | | | | | |
|---|---|---|---|---|---|
| EP | 1511516 | B1 | | 12/2008 | |
| EP | 2020243 | A1 | | 2/2009 | |
| EP | 1511481 | B1 | | 10/2010 | |
| EP | 2020243 | B1 | | 8/2018 | |
| JP | 2007-16024 | A | | 1/2007 | |
| WO | 9841232 | A2 | | 9/1998 | |
| WO | WO-03099278 | A1 | * | 12/2003 | ................ A61P 9/10 |
| WO | 2006032675 | A1 | | 3/2006 | |
| WO | 2006121963 | A2 | | 11/2006 | |
| WO | 2010/141831 | A1 | | 12/2010 | |
| WO | 2015132708 | A1 | | 9/2015 | |
| WO | 2016/152821 | A1 | | 9/2016 | |
| WO | 2017072131 | A1 | | 5/2017 | |
| WO | 2019/130052 | A1 | | 7/2019 | |
| WO | 2020/223279 | A1 | | 11/2020 | |
| WO | 2021100051 | A1 | | 5/2021 | |

OTHER PUBLICATIONS

Liu et al., "Analysis of Th17-associated cytokines and clinical correlations in patients with dry eye disease," PLOS ONE 12(4) (Apr. 5, 2017), 12 pages.

Riemens et al., "Cytokines in tear fluid of patients with ocular graft-versus-host disease after allogeneic stem cell transplantation," Molecular Vision (2012), 18:797-802.

Rajasagi et al., "The Role of T Cells in Herpes Stromal Keratitis," Frontiers in Immunology, (Mar. 2019), vol. 10, Article 512, 7 pages.

Walscheld et al., "Increased Circulating Proinflammatory T Lymphocytes in Children with Different Forms of Anterior Uveitis: Results from a Pilot Study," Ocul Immunol Inflamm. (2019), 27(5):788-797, 2 pages.

Fung et al., "Local delivery of corticosteroids in clinical ophthalmology: A review," Clin. Experiment Ophthalmol. (2020), 48:366-401.

Kaiko et al., "Immunological decision-making: how does the immune system decide to mount a helper T-cell response?," Immunology, (2007); 123(3): 326-338.

Kim et al., "Tear cytokines and chemokines in patients with Demodex blepharitis," Cytokine, 53, (2011), 94-99.

Allergan, Prescribing Information for Pred Forte (prednisolone acetate ophthalmic suspension, USP) 1% sterile (2017), 5 pages.

Agarwal et al., "Formulation Considerations for the Management of Dry Eye Disease," Pharmaceutics, 13, 207 (Feb. 3, 2021), 19 pages.

International Search Report and Written Opinion mailed Feb. 8, 2024 in corresponding International Application No. PCT/US2023/032835 (12 pages).

Loch, et al., "Determination of permeability coefficients of ophthalmic drugs through different layers of porcine, rabbit and bovine eyes", European Journal of Pharmaceutical Sciences 47 (2012) 131-138 (8 pages).

Toropainen, et al., "Biopharmaceutics of Topical Ophthalmic Suspensions: Importance of Viscosity and Particle Size in Ocular Absorption of Indomethacin", Pharmaceutics 2021, 13, 452 (13 pages).

Vazquez-Blanco et al., "pH determination as a quality standard for the elaboration of oral liquid compounding formula", Farmacia Hospitalaria, 2018;42(6):221-227 (7 pages).

Wiley A Chambers, MD. Clinical Review #2. for NOA 208144. Feb. 27, 2017 (Year: 2017).

Kalepu et al., Review. Insoluble drug delivery strategies: review of recent advances and business prospects. Acta Pharmaceutica Sinica B 2015;5(5):442-453 (Year: 2015).

Mohr et al., Gamma irradiation for terminal sterilization of 17b-estradiol loaded poly-(D,L-lactide-co-glycolide) microparticles, Journal of Controlled Release 61 (1999) 203-217 (Year: 1999).

Saricay et al., "Concurrent ocular pain in patients with neurotrophic keratopathy", The Ocular Surface 22 (2021) 143-151 (9 pages).

The extended European search report mailed Sep. 4, 2026 in corresponding European Application No. 23866223.3 (10 pages).

* cited by examiner

| # | Time | Area | Height | Width | Area% | Symmetry |
| --- | --- | --- | --- | --- | --- | --- |
| 1 | 5.26 | 2645.6 | 385.1 | 0.1041 | 100.000 | 0.835 |

| # | Time | Area | Height | Width | Area% | Symmetry |
|---|---|---|---|---|---|---|
| 1 | 5.263 | 2578 | 376.1 | 0.112 | 100.000 | 0.811 |

HIGH CONCENTRATION PHARMACEUTICAL COMPOSITIONS OF ROFLUMILAST FOR OPHTHALMIC DELIVERY

CROSS REFERENCE TO RELATED APPLICATION

The present application claims priority to U.S. Provisional Application No. 63/407,366 filed on Sep. 16, 2022, which is incorporated by reference herein.

FIELD OF THE INVENTION

The present invention relates to pharmaceutically effective ophthalmic compositions having a high concentration of the phosphodiesterase-4 inhibitor, roflumilast. Additionally, the present invention includes methods of treatment by administering said compositions.

BACKGROUND OF THE INVENTION

Roflumilast is a potent and selective long-acting inhibitor of phosphodiesterase (PDE) type 4, with anti-inflammatory and potential antineoplastic activities. Roflumilast is known to be suitable as a bronchial therapeutic agent as well as for the treatment of inflammatory disorders. Compositions containing roflumilast are used in human and veterinary medicine and have been proposed for the treatment and prophylaxis of diseases including but not limited to: inflammatory and allergen-induced airway disorders (e.g., bronchitis, asthma, COPD), dermatoses (e.g., proliferative, inflammatory, and allergen induced skin disorders), and generalized inflammations in the gastrointestinal region (Crohn's disease and ulcerative colitis). Oral pharmaceutical compositions of roflumilast are currently marketed under the tradenames Daliresp® (in the United States) and Daxas® (in Europe), and topical compositions of roflumilast cream for dermatological use are currently marked under the tradename Zoryve™ (in the United States).

Roflumilast and its synthesis are described in U.S. Pat. No. 5,712,298. It has been recognized that pharmaceutical compounds having phosphodiesterase (PDE)-4 inhibiting properties, such as roflumilast, are therapeutically effective and useful for treating inflammatory disorders, such as psoriasis and atopic dermatitis. While the therapeutic effectiveness of oral and dermal pharmaceutical compositions have been studied, there is a need for high concentration ophthalmic pharmaceutical compositions of roflumilast suitable for treating inflammatory and immune-mediated disorders of the eye, particularly for delivery to the anterior and posterior compartments of the eye, or into the tissues or chambers surrounding the eye. The majority of the market for anti-inflammatory ophthalmic drugs today is based around antibiotics, immunosuppressants and steroids, many of which either do not meet the clinical needs of long-term inflammatory disease, or which present significant long-term comorbidity and safety issues. As such, there is a high unmet need for an anti-inflammatory roflumilast ophthalmic formulation in a convenient and tolerable form, suitable for the ocular surface, anterior, or vitreous/posterior compartments of the eye. The majority of the market for high concentration agents suitable for delivery to the anterior or posterior (also called vitreous and or retina) compartment of the eye are focused on mechanisms outside of inflammation (for example, anti-angiogenic agents), anti-inflammatory steroids that are available in high concentration or long-acting formulations by format of a polymer implant or depot to the back of the eye, or systemic biologic agents targeted to single inflammatory pathways, such as TNF. While some anti-inflammatory ophthalmic agents can be used in injectable or other forms for acute use in post-surgical or post-procedural settings, there are very limited long-term options, which are both efficacious and avoid the safety concerns of steroidal agents. Further limiting the market, many anti-inflammatory pharmacotherapies traditionally used in the ocular surface or anterior chamber (the front of the eye) for mid to long-term use are either too large in molecular weight for ophthalmic delivery or unpredictable in ophthalmic tissue compartment pharmacokinetics (PK) to be consistently used in the interior, posterior, and vitreous compartment of the eye.

The delivery of drugs locally to the eye is very difficult, as pharmaceutical ophthalmic agents must balance tolerability, sterility, safety, and efficacy. Developing a stable ophthalmic formulation, which can be made under sterile conditions while retaining physico-chemical properties, staying within a tight range of pH and inactive ingredients which are tolerable to the eye, and which can be delivered in effective doses to the eye, is very difficult. Excipients used for ophthalmic delivery can potentially exhibit ocular toxicity and further exacerbate disorders and associated symptoms of the treated disorder. Development of high concentration pharmaceutical compositions for ophthalmic delivery can be particularly difficult because of physical limitations. Ophthalmic delivery is focused on either the ocular surface, the anterior, or posterior/vitreous segment of the eye. Ocular surface formulations, often delivered by the patient as an eye drop, one to four times a day (or more, in the case of tapered steroids), have the additional challenge of requiring dosing consistency and yet flexibility to deliver effective dose despite common operator errors found in home-based patient delivery: sterility issues, variance in delivery volume, patient compliance, and accuracy in placement. Patients with long-term ocular disease also have increased sensitivity to active and inactive ingredients and preservatives, creating additional formulation challenges. Most high concentration agents intended for interior ophthalmic use within the anterior or posterior/vitreous compartments must typically be delivered via injection into various relevant tissues or chambers, which present unique challenges from those of ocular surface delivery. Because of the small overall size of the ocular compartments, the volume of product delivered must be highly limited, typically to a preferred volume of 50-100 µl, with a maximum safe volume of approximately 200 µL without pre-injection paracentesis. When accessing the interior compartments of the eye via injection, regardless of the site of injection, it is desired to limit the number of applications (injections) to minimize risk to the patient of introducing infectious agents, and to limit physical stress to the sites of injection, particularly when treating chronic conditions. There is also a need for concentrated formulations for injection into the tissues and chambers surrounding the orbit of the eye, to minimize frequency of injection.

The need for a very small injection volume, and high enough drug payload within that small injection volume to limit the frequency of injections, creates the need for a higher concentration drug for use in many ophthalmic disorders. Injections are also limited to physician administration, causing a convenience burden for both patient and physician office.

SUMMARY OF THE INVENTION

The present invention relates to high concentration ophthalmic pharmaceutical compositions of the phosphodiesterase-4 inhibitor, roflumilast. In certain embodiments, the ophthalmic pharmaceutical formulation comprise about 2% to about 5% w/v of roflumilast, a viscosity agent, a tonicity agent, a buffer agent, a surfactant, and water. The ophthalmic pharmaceutical composition is suitable for intravitreal or other injection-based administration into targeted tissues in the eye, or into the tissues or chambers surrounding the eye or orbit. In certain embodiments, the ophthalmic pharmaceutical composition comprises a viscosity agent selected from the group consisting of hydroxypropyl methylcellulose, polyvinylpyrrolidone, or sodium carboxymethyl cellulose. In certain embodiments, the tonicity agent comprises one or more of sodium chloride and potassium chloride. In certain embodiments, the ophthalmic pharmaceutical composition further comprises a buffer agent, preferably acetate and citrate buffers (e.g., sodium acetate and sodium citrate). In certain embodiments, the ophthalmic pharmaceutical composition further comprises a surfactant, preferably a polysorbate (e.g., polysorbate 20). In certain embodiments, the pH of the composition is between 5.5 to 7.5.

In certain embodiments, the ophthalmic pharmaceutical composition comprises about 2% to about 5% w/v of roflumilast, about 0.2% to about 0.8% w/v of sodium carboxymethyl cellulose, about 0.2% to about 0.8% w/v of sodium chloride, about 0.02% to about 0.25% w/v of polysorbate 20, about 0.005% to about 0.20% w/v of potassium chloride, about 0.005% to about 0.20% w/v of calcium chloride, about 0.005% to about 0.20% w/v of magnesium chloride, about 0.005% to about 0.20% w/v of sodium acetate, about 0.005% to about 0.20% w/v of sodium citrate, and water. The ophthalmic pharmaceutical composition is suitable for intravitreal administration or other injection-based administration into the eye, or into the tissues or chambers surrounding the eye. In certain embodiments, the pH of the composition is between 5.5 and 7.5.

In certain embodiments, the pharmaceutical composition has a particle size distribution characterized by a d90 value of less than or equal to about 20 μm. In certain embodiments, the pharmaceutical composition has a particle size distribution characterized by a d90 value of less than or equal to about 15 μm. In certain embodiments, the pharmaceutical composition has a particle size distribution characterized by a d90 value of less than or equal to about 10 μm.

In certain embodiments, the pharmaceutical composition is capable of being injected from a 27 G syringe needle with a force of less than about 3.00 N. In certain embodiments, the pharmaceutical composition is capable of being injected from a 30 G syringe needle with a force of less than about 3.50 N.

In certain embodiments, the ophthalmic pharmaceutical composition comprises or contains a low amount of impurities. In certain embodiments, the pharmaceutical composition has less than about 0.5%, less than about 0.2%, or essentially 0% impurities after terminal sterilization (e.g., gamma irradiation). The gamma-dose rate, applied dose, and time affect the molecular structure of an irradiated sample in various ways because irradiation can affect the chemical and physical structures of the drug, formulation excipients, and packaging materials. Gamma radiation is an ionizing sterilization process in which a sample is exposed to gamma rays to eliminate microorganisms that could be present. According to ISO 11137, a common dose for irradiation sterilization is 25-40 kGy. The accuracy and effects of gamma irradiation are important to consider during sterilization procedures, especially for intravitreal or other injections. Dose distribution and uncertainty should be recorded with several dosimeters in the medicinal product sample tray to confirm the sterilization procedure is reliable and reproducible. The uncertainty of uniform radiation must be lower than 10%, statistically speaking, to conclude that a batch or sample has been uniformly irradiated.

Typical dose mapping procedure involves placing a tray with injectable product samples on a stand located centrally in a gamma-ray generating sample chamber. At least two dosimeters are placed on the samples, one over and other under tray. Minimum (Dmin) and maximum dose (Dmax) estimations are conducted, in addition to a separate monitoring dosimeter (Dmon) usually placed above the sample tray. Dosimeter placement and measurements should be repeated according to ISO 11137-3. Dmin, Dmax, and Dmon are calculated as an average of performed measurements.

In certain embodiments, a method for treating an eye disorder in a patient is provided. The method can comprise injecting a high concentration ophthalmic pharmaceutical composition of roflumilast into the eye of the patient. In certain embodiments, the pharmaceutical composition is one of the compositions described herein and comprises about 2% to about 5% w/v of roflumilast. In certain embodiments, the eye disorder is selected from the group consisting of anterior, posterior, pan or intermediate uveitis; or uveitis associated with HLA-B27, juvenile idiopathic arthritis, Behcets disease, ankylosing spondylitis, Vogt-Koyanagi-Harada Syndrome (VKH), or autoimmune disease; ocular graft vs host disease, Stevens-Johnson syndrome/toxic epidermal necrolysis (TENS), diabetic retinopathy, diabetic macular edema, retinal vein occlusion, age-related macular degeneration (AMD) including dry, geographic atrophy, or exudative AMD, choroidal neovascularization, retinal vasculitis (drug related/iatrogenic, non-infectious/sterile, or idiopathic), choroidal thickening associated with thyroid eye disease, Coats' disease, central serous retinopathy or chorioretinopathy, sterile or infectious endopthalmitis, retinitis, choroiditis, anterior or posterior sclertis/episcleritis, endothelial keratitis (bacterial, viral, fungal, or non-infectious in nature), and other inflammatory diseases of the anterior and posterior tissues of the eye or ocular complications of other inflammatory or autoimmune diseases, inflammation associated with inherited retinal diseases, retinitis pigmentosa, Stargardt disease, Leber congenital amaurosis, Leber hereditary optic neuropathy, Usher syndrome, X-linked retinoschisis, choroidemia, zonal occult outer retinopathy, myopia, vitreomacular adhesion, retinal detachment, choroidal detachment and hemorrhage, choroidal rupture, choroidal folds, proliferative vitreoretinopathy, idiopathic ischemia, achromatopsia, retinopathy of prematurity, gyrate atrophy, central areolar choroidal dystrophy, punctate inner choroidopathy, multifocal choroiditis, choroiditis, choroidal granuloma, choroidal dystrophy, choroidal fibrosis, acute posterior multifocal placoid pigment epitheliopathy, serpiginous choroidopathy, birdshot retinochoroidopathy, multiple evanescent white dot syndrome, retinoblastoma, choroidal melanoma, retinal lymphoma, and iatrogenic posterior or vitreous chamber inflammation. In certain embodiments, the pharmaceutical composition delivers a therapeutic level of roflumilast to one or more of the cornea, limbus, conjunctiva, eyelids, lacrimal and Meibomian glands, lens, pupil, iris, anterior sclera, ciliary body, lacrimal glands, aqueous humor, the internal or endothelial or inner layer of the cornea, lacrimal glands, lymph nodes, posterior sclera, retina, choroid, macula, fovea, optic disc, optic nerve, vitreous humor, or hyaloid canal.

BRIEF DESCRIPTION OF THE DRAWINGS

The accompanying drawings, which are incorporated herein and form part of the disclosure, help illustrate various embodiments of the present invention and, together with the description, further serve to describe the invention to enable a person skilled in the pertinent art to make and use the embodiments disclosed herein. The error bars in the drawings are standard deviation values.

DETAILED DESCRIPTION OF THE INVENTION

Figure 1:
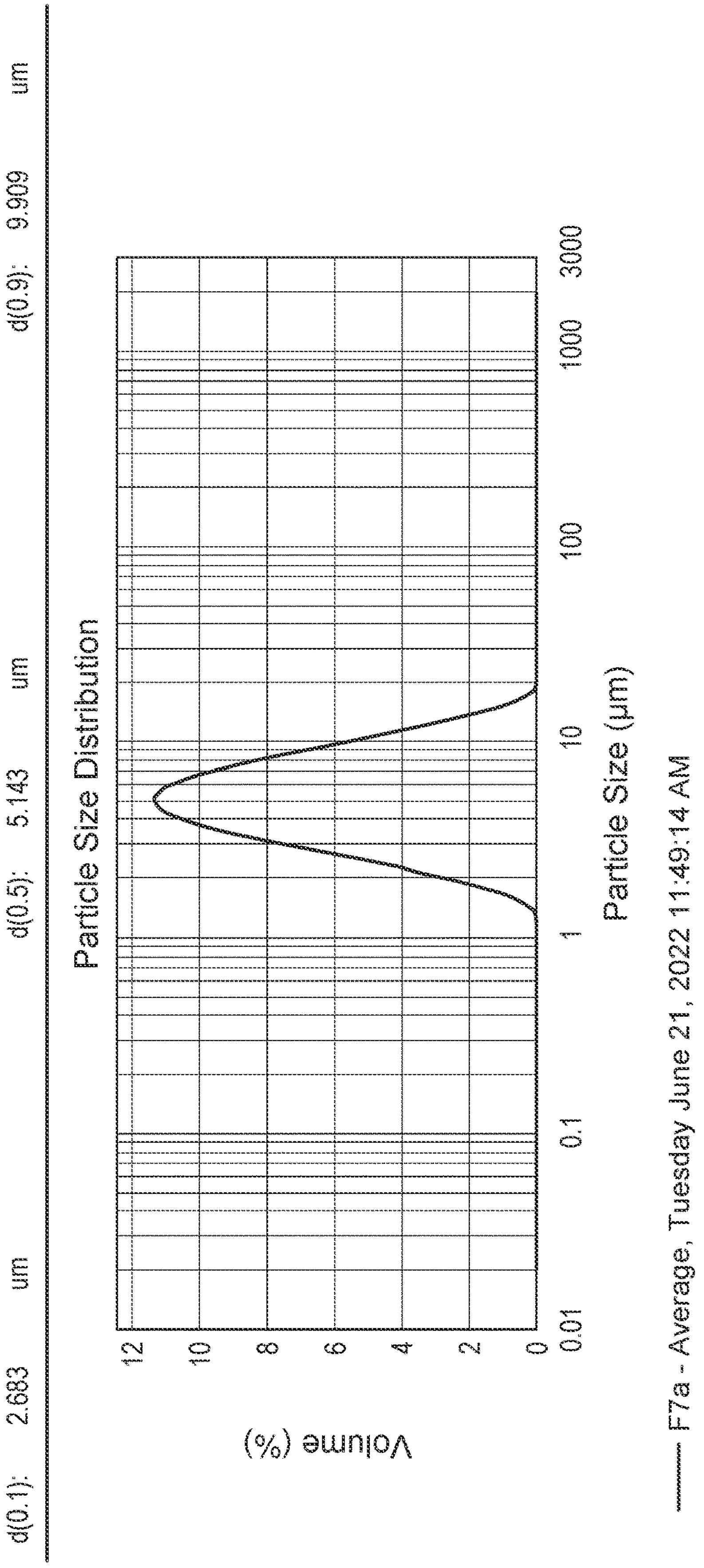
FIG. 1 is a particle size distribution plot (time versus particle size in μm) for an ophthalmic pharmaceutical composition of an exemplary pharmaceutical composition prior to gamma irradiation.

It is to be understood that the invention is not limited to the particular methodology, protocols, and reagents described herein as these may vary. It is also to be understood that the terminology used herein is for the purpose of describing particular embodiments only and is not intended to limit the scope of the present invention which will be limited only by the appended claims. Unless defined otherwise, all technical and scientific terms used herein have the same meanings as commonly understood by one of ordinary skill in the art to which this invention belongs.

All publications, patents and patent applications cited herein are hereby incorporated by reference in their entirety unless otherwise stated. Where the same term is defined in a publication, patent, or patent application and the present disclosure incorporated herein by reference, the definition in the present disclosure represents a controlling definition. For publications, patents and patent applications referenced to describe a particular type of compound, chemistry, etc., the portion relating to such compounds, chemistry, etc. is the portion of the literature incorporated herein by reference.

Note that as used herein, the singular forms "a," "an," and "the" include plural referents unless the context clearly dictates otherwise. Thus, for example, "active ingredient" includes a single ingredient and two or more different ingredients.

The term "about" when used in connection with a numerical value is meant to encompass numerical values within a range having a lower limit that is 5% smaller than the indicated numerical value and having an upper limit that is 5% larger than the indicated numerical value.

The term "ocular surface" refers to tissues at or near the surface of the eye, including cornea, conjunctiva, or tear film. The term "anterior chamber" or "anterior chamber ocular disease" refers to the tissues relevant to, and disease affecting the anterior or front chamber of the eye through the iris ciliary body and lens, anterior sclera, aqueous humor, and the endothelial or internal-most layer of the cornea. Anterior ocular diseases are in contrast to vitreous chamber, posterior tissues, or ocular diseases, such as those affecting the retina, and distinct from the ocular surface or those directly impacting external environment facing tissues such as the corneal conjunctival tissues, or the ocular surface and tear film. The term "vitreous chamber" or "vitreous chamber ocular disease" refers to the tissues relevant to, or disease affecting the vitreous chamber located from the posterior of the lens, through and including retina and choroid, vitreous humor, posterior sclera, and to the optic nerve. The terms "extraorbital" or "tissues or chambers surrounding the eye" refers to tissues relevant to the external surface of the eye or the eyelid and surrounding tissues or the muscle around the eye or orbit, or the space behind the eye, or to diseases related to these tissues and chambers.

The term "eye disorder," "eye condition," or "ocular disorder," refer to diseases/conditions of the eye(s) that can be sight-threatening, lead to eye discomfort or disturbance, and may signal systemic health problems. The ocular surface is composed of the cornea (including particularly the corneal epithelium and stroma), limbus, conjunctiva, eyelids, lacrimal and Meibomian glands, and the interconnecting surface nerves. The anterior chamber is made up of the lens, pupil, iris, anterior sclera, ciliary body, lacrimal glands, aqueous humor, and the internal or endothelial or inner layer of the cornea, lacrimal glands and lymph nodes. The vitreous chamber is made up of the posterior sclera, retina, choroid, macula, fovea, optic disc, optic nerve, vitreous humor, and hyaloid canal. The eye as a whole is supported by the various in-eye and extra-orbital muscles and ligaments, which make up the extra-orbital space.

The term "effective" refers to an amount of a compound, agent, substance, formulation or composition that is of sufficient quantity to result in a decrease in severity of disease symptoms, an increase in frequency and duration of disease symptom-free periods, or a prevention of impairment or disability due to the disease affliction. The amount may be as a single dose or according to a multiple dose regimen, alone or in combination with other compounds, agents or substances. One of ordinary skill in the art would be able to determine such amounts based on such factors as a subject's size, the severity of a subject's symptoms, and the particular composition or route of administration selected.

"Pharmaceutically acceptable" means generally safe for administration to humans or animals. Preferably, a pharmaceutically acceptable component is one that has been approved by a regulatory agency of the Federal or a state government or listed in the U.S. Pharmacopeia, published by the United States Pharmacopeial Convention, Inc., Rockville Md., or other generally recognized pharmacopeia for use in animals, and more particularly in humans.

A "pharmaceutical composition" according to the invention may be present in the form of a composition, wherein the different active ingredients and diluents and/or carriers are admixed with each other, or may take the form of a combined preparation, where the active ingredients are present in partially or totally distinct form. An example for such a combination or combined preparation is a kit-of-parts.

The term "roflumilast" as used in this application refers to roflumilast, its physical form, its salts, the metabolites of roflumilast including roflumilast N-oxide, and its salts unless specified otherwise or unless it is clear in context that reference is to roflumilast itself.

As used herein, the terms "subject" "or patient" most preferably refers to a human being. The terms "subject" or "patient" may include any mammal that may benefit from the compounds described herein.

A "therapeutic amount" or "therapeutically effective amount" is an amount of a therapeutic agent sufficient to achieve the intended purpose. The effective amount of a given therapeutic agent will vary with factors such as the nature of the agent, the route of administration, the size of the subject to receive the therapeutic agent, and the purpose of the administration. The effective amount in each individual case may be determined empirically by a skilled artisan according to established methods in the art.

As used herein, "treat," "treating," or "treatment" of a disease or disorder means accomplishing one or more of the following: (a) reducing the severity and/or duration of the disorder; (b) limiting or preventing development of symptoms characteristic of the disorder(s) being treated; (c) inhibiting worsening of symptoms characteristic of the disorder(s) being treated; (d) limiting or preventing recurrence of the disorder(s) in patients that have previously had the disorder(s); and (e) limiting or preventing recurrence of symptoms in patients that were previously symptomatic for the disorder(s).

The present invention relates to stable ophthalmic pharmaceutical compositions of the phosphodiesterase-4 inhibitor, roflumilast. Roflumilast is a compound of the formula (I):

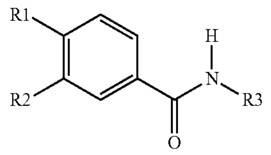

(I)

wherein R1 is difluoromethoxy, R2 is cyclopropylmethoxy and R3 is 3,5-dichloropyridin-4-yl.

Roflumilast has the chemical name N-(3,5-dichloropyridin-4-yl)-3-cyclopropylmethoxy-4-difluoromethoxybenzamide. The N-oxide of roflumilast has the chemical name 3-cyclopropylmethoxy-4-difluoromethoxy-N-(3,5-dichloropyrid-4-yl 1-oxide) benzamide. Roflumilast and its synthesis, the use of roflumilast as a phosphodiesterase (PDE) 4 inhibitor, and roflumilast formulations, were described in U.S. Pat. No. 5,712,298, which is incorporated herein by reference. The ophthalmic pharmaceutical composition can include roflumilast as a free base or a pharmaceutically acceptable salt. Exemplary salts of roflumilast are salt described in paragraphs [0012] and [0013] of U.S. Patent Application Publication No. US 2006/0084684, the disclosure of which is incorporated herein by reference. In certain embodiments, the pharmaceutical composition comprises a metabolite of roflumilast, including the N-oxide of the pyridine residue of roflumilast or salts thereof, as an active ingredient.

In certain embodiments, the ophthalmic pharmaceutical composition can comprise roflumilast in a range from about 2.0% w/v to about 6.5% w/v, or from about 2.0% w/v to about 5.5% w/v, or from about 2.0% to about 5.0% w/v. For example, the ophthalmic pharmaceutical comprises any of the following w/v percents of roflumilast: 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, etc.

In certain embodiments, the ophthalmic pharmaceutical composition can be a suspension, solution, emulsion, eye drop, eye ointment, cream, gel, a spray, an injectable formulation (intravitreal, sub-conjunctival, suprachoroidal, subtenon, periocular, peribulbar, retrobulbar, retro-orbital, or other injections), a depot formulation (whether alone or in conjunction with a depoting agent or device), an implantable absorbable polymeric device or an adsorbent contact lens. In certain embodiments, the pharmaceutical composition is intravitreal, sub conjunctival, sub retinal, intracameral, subtenon, periocular, peribulbar, retrobulbar, retro-orbital, suprachoroidal injection, delivery via port or drug-eluting material, cannula delivery, needle delivery, or other injection site and delivery methods.

It has been shown through literature that high concentration ophthalmic pharmaceutical compositions such as steroids or other agents formulated for use intravitreally or other injection internal to the orbit can also be administered via injection externally to the surrounding tissues. T. Ciuella et al., Microinjection via the Suprachoroidal Space: A Review of a Novel Mode of Administration. Am. J. Manag. Care, 28(13 Suppl.):5242-252 (2022); L. Naftali Ben Haim et al., Drug Delivery to the Suprachoroidal Space for the Treatment of Retinal Diseases, Pharmaceutics 13(7):967 (2021); A. Hadayer, Delivery of Steroids into the Eye for the Treatment of Macular Edema, Expert Opn. Drug Deliv., 13(8):1083-1091 (2016); T. Yasukawa et al., Recent Advances in Intraocular Drug Delivery Systems, Recent Pat. Drug. Deliv. Formul., 5(1)-1-10 (2011). Administration externally to the surrounding tissues can be done by using the same delivery device, for example a 27-gauge or 30-gauge needle as disclosed herein. See Tomas Ortiz-Basso, et al., Triamcinolone for the Treatment of Ophthalmopathy Tested with Short Tau Inversion Recovery Magnetic Resonance, Ophtal. Plast. Reconstr. Surg., Vol. 35, No. 1 (2019); Ayman Alkawas et al., Orbital Steroid Injection Versus Oral Steroid Therapy in Management of Thyroid-Related Ophthalmopathy, Clinical and Experimental Ophthalmology, 38:692-697 (2010).

In certain embodiments, the pharmaceutical composition may be in the form of an implant such as intravitreal implants, transscleral implants, extended release implants, biodegradable or nonbiodegradable implant materials, bioadhesive polymers, hydrogels, nanoparticles, viral vectors, adhesive spheres, micelles, microspheres, thermogels, liposomes, nanoliposomes, lipid nanoparticles, extracellular vesicles, exosomes, thermogels, mucoadhesive gels, crystals, microemulsions, nanoemulsions, emulsions, dendrimers, polyvinyl alcohol (PVA), ethylene-vinyl acetate (EVA), silicones, poly(ethylene glycol) (PEG), crosslinked poly (ethylene glycol) (PEG), poly(lactic-co-glycolic acid) (PLGA), poly-glycolic acid (PGA), and poly(caprolactones) (PCL), polyethylene terephthalate (PET), polyimide, antibodies, collagen, hyaluronic acid, extracellular matrix, silica or silicon matrix, or any combination thereof. In preferred embodiments, the pharmaceutical composition is a suspension suitable for intravitreal, suprachoroidal, or subtenon administration, wherein the active ingredient (i.e., roflumilast) is suspended in a pharmaceutical carrier and/or excipients. In certain embodiments, the roflumilast is a free-flowing re-suspendable suspension suitable for intravitreal administration or other injection.

In certain embodiments, the ophthalmic pharmaceutical composition comprises a viscosity agent, a tonicity agent, a buffer, and water. In certain embodiments, the pharmaceutical composition further comprises a surfactant. In certain embodiments, the ophthalmic pharmaceutical composition can include one or more additional excipients, including for example, a stabilizer, a preservative, a wetting agent, a diluting agent, a pH adjuster, or an absorption enhancer. In certain embodiments, the ophthalmic pharmaceutical composition can also be utilized for anterior or vitreous/posterior ophthalmic situations in the form of an injection (intravitreal, suprachoroidal, or other) as a depot, an implantable adsorbent polymeric device for any ophthalmic or surrounding tissue placement, an in situ forming gel, or a drug/device combination, wherein the active ingredient (i.e., roflumilast) is suspended with one or more of the excipients above, for example a viscosity agent, a polymer (i.e., PLGA), a surfactant, or a buffer; with or without a device or inert depot compound.

In certain embodiments, the viscosity agent is a cellulose derivative. In certain embodiments, the viscosity agent is at least one selected from the group consisting of sodium carboxymethyl cellulose, hydroxypropyl methylcellulose (HPMC), hydroxyethylcellulose (HEC), carboxymethyl cellulose (CMC), or methylcellulose. In certain embodiments, the viscosity agent is polyvinylpyrrolidione or povidone (PVP), hypromellose (HPMC), or polyvinyl alcohol (PVA). In certain embodiments, the viscosity agent is a dextran or gelatin. In addition, the viscosity agent can include a carbomer in certain embodiments, such as a carbomer copolymer Type A or a carbomer copolymer Type B including those marketed under the trade name Carbopol® by Lubrizol®. In certain embodiments, the ophthalmic pharmaceutical formulation can comprise a viscosity agent in a range from about 0.1% w/v to about 5.0% w/v, or from about 0.1% w/v to about 4.0% w/v, or from about 0.1% w/v to about 3.0% w/v, or from about 0.1% w/v to about 2.0% w/v, or from about 0.1% to about 1.0% w/v, or from about 0.1% to about 0.8% w/v, or from about 0.2% to about 1.0% w/v, or from about 0.2% to about 0.8% w/v. For example, the ophthalmic pharmaceutical comprises any of the following w/v percents of a viscosity agent: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, etc.

In certain embodiments, the tonicity agent is at least one selected from the group consisting of sodium chloride, potassium chloride, glycerin, and dextrose. In preferred embodiments, the tonicity agent is at least one selected from the group consisting of sodium chloride and potassium chloride. In certain embodiments, the ophthalmic pharmaceutical formulation can comprise a tonicity agent in a range from about 0.05% w/v to about 3.0% w/v, or from about 0.05% w/v to about 2.0% w/v, or from about 0.05% to about 1.0% w/v, or from about 0.1% to about 0.8% w/v, or from about 0.1% to about 0.5% w/v, or from about 0.2% to about 0.8% w/v, or from about 0.2% to about 0.5% w/v. For example, the ophthalmic pharmaceutical comprises any of the following w/v percents of a tonicity agent: 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, etc.

In certain embodiments, the surfactant is at least one selected from the group consisting of polysorbates (including, polysorbate 20, polysorbate 40, polysorbate 60, and polysorbate 80) and tyloxapol. In certain embodiments, the ophthalmic pharmaceutical formulation can comprise a surfactant in a range from about 0.02% w/v to about 3.0% w/v, or from about 0.02% w/v to about 2.5% w/v, or from about 0.02% w/v to about 2.0% w/v, or from about 0.02% to about 1.0% w/v, or from about 0.02% to about 0.5% w/v, or from about 0.02% to about 0.25% w/v. For example, the ophthalmic pharmaceutical comprises any of the following w/v percents of a surfactant: 0.02%, 0.05%, 0.075%, 0.1%, 0.15%, 0.2%, 0.25%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, etc.

In certain embodiments, the buffer is at least one selected from the group consisting of citrate, phosphate, Tris-HCl (Tris), acetate, and borate buffers. In certain embodiments, the ophthalmic pharmaceutical formulation can comprise a buffer in a range from about 0.5% w/v to about 7.5% w/v, or from about 0.5% w/v to about 5.0% w/v, or from about 0.5% to about 3.0% w/v, or from about 0.5% w/v to about 2.0% w/v, or from about 0.5% to about 1.0% w/v. For example, the ophthalmic pharmaceutical comprises any of the following w/v percents of a buffer: 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 7%, 1.8%, 1.9%, 1.0%, 2.1%, 2.2%, 2.3%, 2.4%, 2.5%, 2.6%, 2.7%, 2.8%, 2.9%, 3.0%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, etc.

In certain embodiments, the ophthalmic pharmaceutical formulation does not include any preservatives or anti-microbial agents, as most ophthalmic preservatives and anti-microbial agents are known to cause patient discomfort, burning, stinging, or irritation.

Roflumilast can undergo hydrolysis in certain ophthalmic pharmaceutical compositions and under certain standard sterile manufacturing processes. In certain embodiments, the pH of the ophthalmic pharmaceutical compositions is adjusted to reduce the rate of hydrolysis of roflumilast.

In certain embodiments, the osmolality of the ophthalmic pharmaceutical composition is about 250 mOsm/kg to 330 mOsm/kg, more preferably about 270 mOsm/kg to about 300 mOsm/kg, and even more preferably 270 mOsm/kg to 280 mOsm/kg.

The ophthalmic pharmaceutical compositions of the present invention are stable and exhibit a particle size distribution suitable for ophthalmic delivery. Particle size of the ophthalmic pharmaceutical composition for suspensions can be assessed using laser diffraction methods. Laser diffraction is recognized by standards and guidance agencies including ISO and ASTM and is widely used to determine particle size distributions. In conducting the assessment, the sample is passed through a laser beam, which results in laser light scattered at a range of angles. Detectors placed at fixed angles measure the intensity of light scattered at that position. A mathematical model is then applied to generate a particle size distribution.

In particle size determinations, the median value is defined as the value where half of the population resides above this point, and half resides below this point. For particle size distributions the median is called the D50. The D50 is the size that splits the distribution with half above and half below this diameter. The distribution width may also be characterized by citing one, two or three values on the x-axis, typically some combination of the D10, D50, and D90. The D50 (or the median), as discussed above, refers to the diameter wherein half of the population lies below this value. Similarly, 90 percent of the distribution lies below the D90, and 10 percent of the population lies below the D10.

In certain embodiments of the present invention, the ophthalmic pharmaceutical composition exhibits a particle size distribution characterized by a d90 value of less than or equal to about 50 μm prior to preferential processing. In certain embodiments, the ophthalmic pharmaceutical composition exhibits a particle size distribution characterized by a d90 value of from about 5 μm to about 25 μm. In certain embodiments, the pharmaceutical compositions exhibits a particle size distribution characterized by a d90 value of from about 5 μm to about 15 μm. In certain embodiments, the pharmaceutical compositions exhibits a particle size distribution characterized by a d90 value of less than or equal to 20 μm. In certain embodiments, the pharmaceutical compositions exhibits a particle size distribution characterized by a d90 value of less than or equal to 15 μm. In preferred embodiments, the pharmaceutical compositions exhibit a particle size distribution characterized by a d90 value of less than or equal to 10 μm.

In certain embodiments of the present invention, the ophthalmic pharmaceutical composition is stable and is free of impurities or has limited impurities. In certain embodiments, the pharmaceutical composition has less than about 1.0%, or less than about 0.5%, or less than about 0.2%, or essentially 0% impurities after terminal sterilization (e.g., gamma irradiation or dry heat sterilization). The amount of impurities can be assessed using an HPLC assay.

The ophthalmic pharmaceutical composition can be administered via a syringe needle for intravitreal administration. In certain embodiments, the ophthalmic pharmaceutical composition is easily injected from a syringe needle with minimal force. In certain embodiments, the pharmaceutical composition is capable of being injected from a 27 Gauge (G) syringe needle with a 0.41 mm outer diameter with a force of less than about 3.00 N. In certain embodiments, the pharmaceutical composition is capable of being injected from a 30 Gauge (G) syringe needle with a 0.31 mm outer diameter with a force of less than about 3.50 N. Given the ease of injection with minimal force in both 27 and 30 gauge it is reasonable to expect that both a smaller gauge needle (30 to 33 Gauge) or a larger gauge needle (25 to 27 Gauge) would be appropriate for use.

The inventors of the subject application have identified that roflumilast in combination with multiple viscosity agents undergoes particle size growth and aggregation in certain heat transferring ophthalmic pharmaceutical manufacturing processes designed to sterilize a formulation. The inventors of the subject application have discovered certain methods of avoiding this aggregate causing heat transfer during sterile processing of the roflumilast in the same vessel as the inactive ingredients including the excipients, surfactants, etc., which can reduce the rate of particle size growth and aggregation while maintaining product potency. Mixing both sterile API with sterile inactives reduces particle aggregation by reducing the need for additional energy inputs like autoclaving, which can cause particle aggregation. In certain embodiments, slow dry heat sterilization at a temperature less than the melting point of roflumilast, gamma radiation, or other methods of sterilization of API can be used to sterilize the roflumilast while standard autoclaving can be used to sterilize the inactives before creating the final mixed formulation for an ophthalmic pharmaceutical composition which is optimized in potency, purity, and particle size, ideal for use in the eye.

In certain embodiments of the present invention, the sterility and safety of the product can be ensured via terminal sterilization followed by sterility testing. With the pharmaceutical compositions listed herein, a dry heat or gamma or x-ray radiation can provide assurance of sterility, followed by sterility testing. The accuracy and extent of the gamma radiation is validated via dosimeter recordings of total radiation experienced in all quadrants of the gamma chamber. Further, sterility can be tested via standard two-week screening post sterilization. The inventors have assessed both non-clinical and clinical batches in this manner, both validating adequate terminal sterilization as well as clearing two-week sterility testing with no microbial growth. Additionally, the injectable product can be controlled for endotoxins. In certain embodiments, the final injectable product can have less than 1 Endotoxin Units per milliliter (i.e., <1 EU/ml).

Terminal sterilization can be used for a pharmaceutical composition by injection, because the composition will be directly injected into the ocular globe or surrounding tissues or chambers (whether sub-conjunctivally, intravitreally, suprachoroidally, peribulbarly, or other site). Terminal sterilization ensures that both the product and the vial are sterile. Needles and syringes which are pre-sterilized are readily available to be used with such a pharmaceutical composition and product configuration. In certain embodiments, the product for injection could also be provided in a pre-filled syringe. In certain embodiments, the resuspendable sterile suspension in crimp-capped vial which would be used with separate, pre-sterilized needles to ensure full-process sterility. The pharmaceutical composition would be resuspended by vortexing, shaking, or mixing to resuspend the suspension, and then the product would be drawn through the pre-sterilized needle prior to injection. The pre-sterilized needle for drawing suspension can be a lower gauge needle which is then replaced with a higher gauge needle for injection (injection typically accomplished with a 27-to-30-gauge needle) or the same needle could be used for drawing and injection so long as sterile conditions are maintained.

In certain embodiments of the present invention, a method of manufacturing an ophthalmic pharmaceutical composition of roflumilast is provided. The pharmaceutical composition can include the pharmaceutical compositions described above. The method can include sterilizing the roflumilast using a form of slow dry heat or low-level radiation sterilization. The sterilization can be achieved by slow dry heat sterilization at a temperature less than the melting point of roflumilast (approximately 159.7° C.), terminal gamma radiation, or other methods of sterilization. The method can further include sterilizing at least one inactive ingredient selected from the group consisting of a viscosity agent, tonicity agent, surfactant, and buffer using standard autoclaving. The method can further include mixing the sterilized roflumilast with the sterilized inactive ingredient to prepare a stable ophthalmic pharmaceutical composition of roflumilast. In certain embodiments, the pharmaceutical composition that is prepared is a suspension.

In certain embodiments, the method can further include subjecting the stable ophthalmic pharmaceutical composition of roflumilast to clarity filtration to further mitigate particle size aggregation and to create an optimal suspension. The clarity filtration can be used to produce a stable ophthalmic pharmaceutical composition of roflumilast, wherein the pharmaceutical composition has a particle size distribution characterized by a d90 value of less than or equal to 10 μm, further differentiated for use in the eye, particularly in patients who may have sensitivity to existing ophthalmic agents. The different formulations can react differently to the filtration process due to the differences in creation of aggregates in some formulations.

The ophthalmic pharmaceutical compositions of the present invention can be administered via intravitreal injection or injection into other sites within the eye or surrounding tissues or chambers. The pharmaceutical composition of roflumilast can be administered to the eye of a patient having an eye disorder or eye condition. In certain embodiments, the pharmaceutical compositions disclosed herein are administered as an injection to treat an eye disorder selected from the group consisting of anterior, posterior, pan or intermediate uveitis; or uveitis associated with HLA-B27, juvenile idiopathic arthritis, Behcets disease, ankylosing spondylitis, VKH, or autoimmune disease; ocular graft vs host disease, Stevens-Johnson syndrome/TENS, diabetic retinopathy, diabetic macular edema, retinal vein occlusion, age-related macular degeneration (AMD) including dry, geographic atrophy, or exudative AMD, choroidal neovascularization, retinal vasculitis (drug related/iatrogenic, non-infectious/sterile, or idiopathic), choroidal thickening associated with thyroid eye disease, Coats' disease, central serous retinopathy or chorioretinopathy, sterile or infectious endopthalmitis, retinitis, choroiditis, anterior or posterior sclertis/episcleritis, endothelial keratitis (bacterial, viral, fungal, or non-infectious in nature), and other inflammatory diseases of the anterior and posterior tissues of the eye or ocular complications of other inflammatory or autoimmune diseases, inflammation associated with inherited retinal diseases, retinitis pigmentosa, Stargardt disease, Leber congenital amaurosis, Leber hereditary optic neuropathy, Usher syndrome, X-linked retinoschisis, choroidemia, zonal occult outer retinopathy, myopia, vitreomacular adhesion, retinal detachment, choroidal detachment and hemorrhage, choroidal rupture, choroidal folds, proliferative vitreoretinopathy, idiopathic ischemia, achromatopsia, retinopathy of prematurity, gyrate atrophy, central areolar choroidal dystrophy, punctate inner choroidopathy, multifocal choroiditis, choroiditis, choroidal granuloma, choroidal dystrophy, choroidal fibrosis, acute posterior multifocal placoid pigment epitheliopathy, serpiginous choroidopathy, birdshot retinochoroidopathy, multiple evanescent white dot syndrome, retinoblastoma, choroidal melanoma, retinal lymphoma, and iatrogenic posterior or vitreous chamber inflammation.

In certain embodiments, the ophthalmic pharmaceutical compositions disclosed herein are administered as an injection in the peri-orbital space via local, orbital, peribulbar, or other injections. In certain embodiments, the ophthalmic pharmaceutical compositions disclosed herein are designed to treat eyelid or extra- or peri-orbital pain and inflammation due to trauma, autoimmune disease, microbial infection, or other systemic disease; thyroid eye disease, meibomian gland disorders, blepharitis ocular cicatricial pemphigus, mucous membrane pemphigus, orbital inflamatory pseudotumor, idiopathic or nonspecific orbital inflammation; granulomatosis with polyangiitis (GPA), Wegeners granulomatosis, orbital (including lacrimal gland) sarcoidosis, chalazion, hordeolum, atopic dermatitis of eyelid, ocular rosacea, neuro-myelitis optica, histiocytic orbital lesions, periorbital capillary hemangiomas, or extra-orbital ocular complications of systemic sclerosis, scleroderma, or other autoimmune disease, and other diseases of the peri-orbital space.

Injections may also be used post-surgically to treat pain and inflammation of cataract, LASIK, PRK, PTK, full or partial thickness keratotomy or keratoplasty, glaucoma-related surgical procedures, inflammation related to gene or cell therapy instillation, or other surgical conditions and procedures where inflammation would be a concern and injectable therapeutic intervention is appropriate. The eye disorders treatable by the methods described herein can be acute or chronic. In certain embodiments, the method is used to treat a patient having an inflammatory or immune disorder of the eye. In certain embodiments, the inflammatory or immune disorder can be one of the above-identified disorders.

In preferred embodiments, the eye disorder is posterior, pan or intermediate uveitis; or uveitis associated with HLA-B27, juvenile idiopathic arthritis, Behcets disease, ankylosing spondylitis, VKH, or autoimmune disease; diabetic retinopathy, diabetic macular edema, cystoid macular edema, retinal vein occlusion, age-related macular degeneration including dry, geographic atrophy, or exudative AMD and choroidal neovascularization, thyroid eye disease, sterile or infectious endophthalmitis, and vitreous or posterior chamber iatrogenic inflammation.

In certain embodiments, the pharmaceutical composition is administered as a regimen, such as at regular intervals. For example, a pharmaceutical composition can be administered directly to the ocular surface as a drop or ointment once daily, twice daily, thrice daily, four times daily, once per week, twice per week, three times per week, or four times per week, monthly, as needed (PRN), or used in a treat and extend manner. In certain embodiments, the pharmaceutical composition can be administered as part of a maintenance dose or titrating dose regimen. The pharmaceutical composition can be administered for a prescribed period of time. For example, a pharmaceutical composition can be administered for a period of about two days to at least about six weeks, or until an improvement in the eye condition or disease is observed. Exemplary periods of time for the treatment regimen include one week, two weeks, one month, six weeks, two months, three months, four months, five months, six months, seven months, eight months, nine months, or one year. For example, a pharmaceutical composition can be administered as an injection or as an implantable device, depot, or adsorbable device could be administered once per week, once per month, once every 2, 3, 4, 5, 6, 7, 8, 9, 10, 11, 12, 13, 14, 15, 16 weeks, once per quarter, once every sixth months, as needed (PRN), per physician direction, or per some clinical criteria such as treat and extend or other criteria. The pharmaceutical composition can be administered as an ongoing treatment with no end.

The following examples illustrate certain embodiments of the invention without limitation.

EXAMPLES

While various embodiments have been described herein, it should be understood that they have been presented by way of example only, and not limitation. Thus, the breadth and scope of the present disclosure should not be limited by any of the described exemplary embodiments. Moreover, any combination of the above-described elements in all possible variations thereof is encompassed by the disclosure unless otherwise indicated herein or otherwise clearly contradicted by context.

Example 1

An ophthalmic pharmaceutical composition having the composition set forth in Table 1 was prepared. The vehicle was prepared in a 100 mL glass bottle. Sodium carboxymethyl cellulose was weighed out and added. 90 mL of water for injection was added into the glass bottle. The resultant mixture was stirred until the sodium carboxymethyl cellulose was dissolved. The remaining excipients (except for roflumilast) were added and the mixture was stirred until the excipients were dissolved. Water was added QS to 100 mL. Roflumilast (previously jet-milled) was added to a 20 mL glass vial and 10 mL of the vehicle was added. The suspension was homogenized using a high-shear mixer (Polyton Model PT 10/35) to form a uniform suspension. The mixing time was 2 minutes at a shear rate of 8000 for a set of 30 at controlled room temperature.

TABLE 1

Ophthalmic Pharmaceutical Composition of Roflumilast

| Ingredient | % w/v |
|---|---|
| Roflumilast | 5.0% |
| Sodium carboxymethyl cellulose | 0.50% |
| Sodium chloride | 0.60% |
| Polysorbate 20 | 0.15% |
| Potassium chloride | 0.05% |
| Calcium chloride (dihydrate) | 0.05% |
| Magnesium chloride (hexahydrate) | 0.05% |
| Sodium acetate (trihydrate) | 0.10% |
| Sodium citrate (dihydrate) | 0.10% |
| 1N HCl | Adjust to pH ~6.5 |
| Water for injection | q.s. ad 10.0 mL |

Example 2

Figure 2:
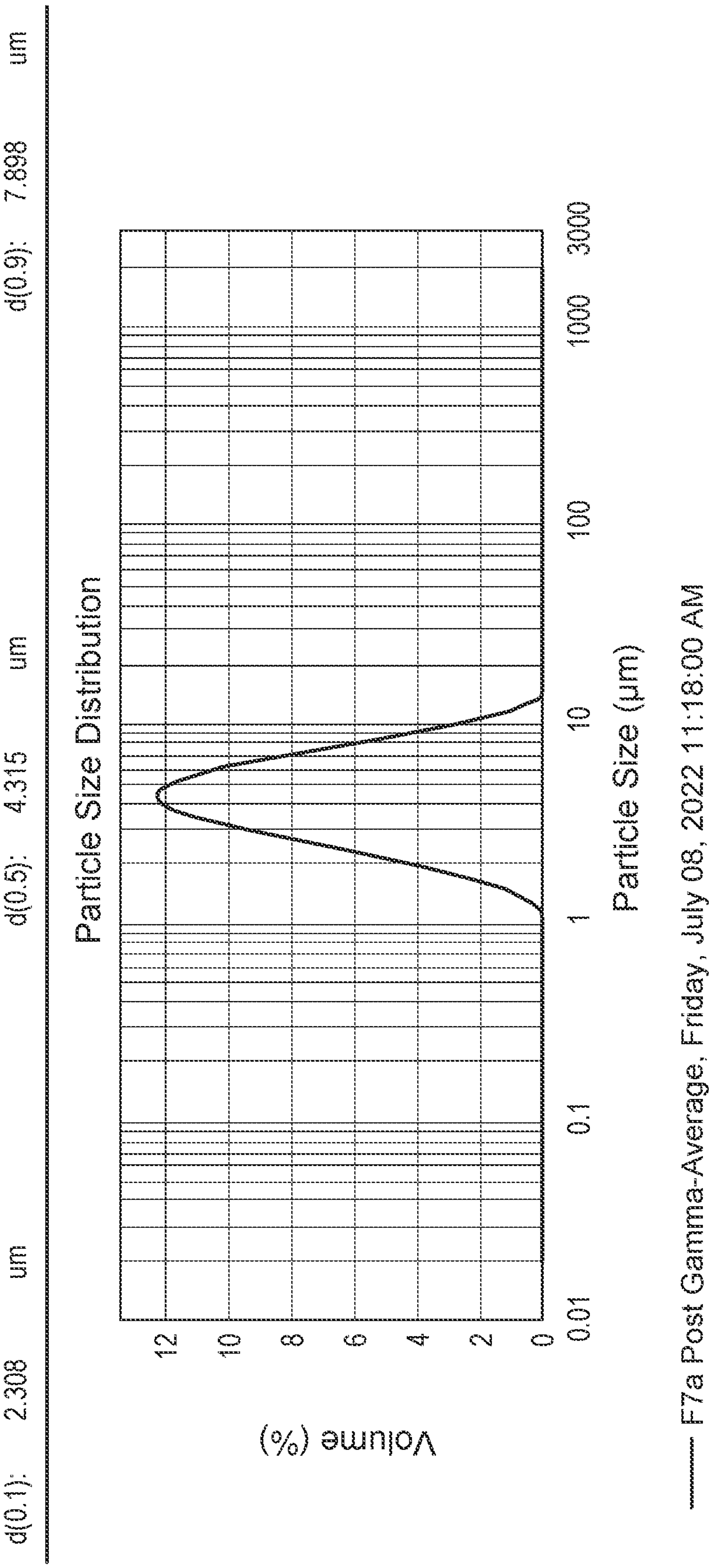
FIG. 2 is a particle size distribution plot (time versus particle size in μm) for an ophthalmic pharmaceutical composition of an exemplary pharmaceutical composition post-gamma irradiation.

The particle size distribution of the ophthalmic pharmaceutical compositions of Example 1 was assessed. The size of particles suspended in liquid vehicle was evaluated using laser light scattering using the Horiba LA-950V2 Particle Size Analyzer. The particle size distribution was assessed pre-gamma irradiation and post-gamma irradiation. The particle size distribution plots are set forth in FIG. 1 (pre-gamma irradiation) and FIG. 2 (post-gamma irradiation). The results are set forth in Table 2.

TABLE 2

Particle Size Assessment

| Sample | Dv10 (μm) | Dv50 (μm) | Dv90 (μm) |
|---|---|---|---|
| Pre-Gamma Irradiation | 2.683 | 5.143 | 9.909 |
| Post-Gamma Irradiation | 2.308 | 4.315 | 7.898 |

Example 3

The injection force required to inject the pharmaceutical composition of Example 1 from a 27 Gauge×½ inch and 30 Gauge×¼ inch syringe needle was assessed. 1 ml of resuspended formulation was drawn into a 1 ml BD syringe and 30 G×½" BD (or 27 G×¼" NIPRO) needle, respectively. The needle is connected to a Kd Scientific Hz 50/60 Force Meter, with the following parameters (1 ml syringe of inner diameter (ID)=4.54 mm, speed=2 ml/min) and the ejection of material started. The injection force required to fully eject the contents of the pharmaceutical composition are measured by the force meter.

Figure 3:
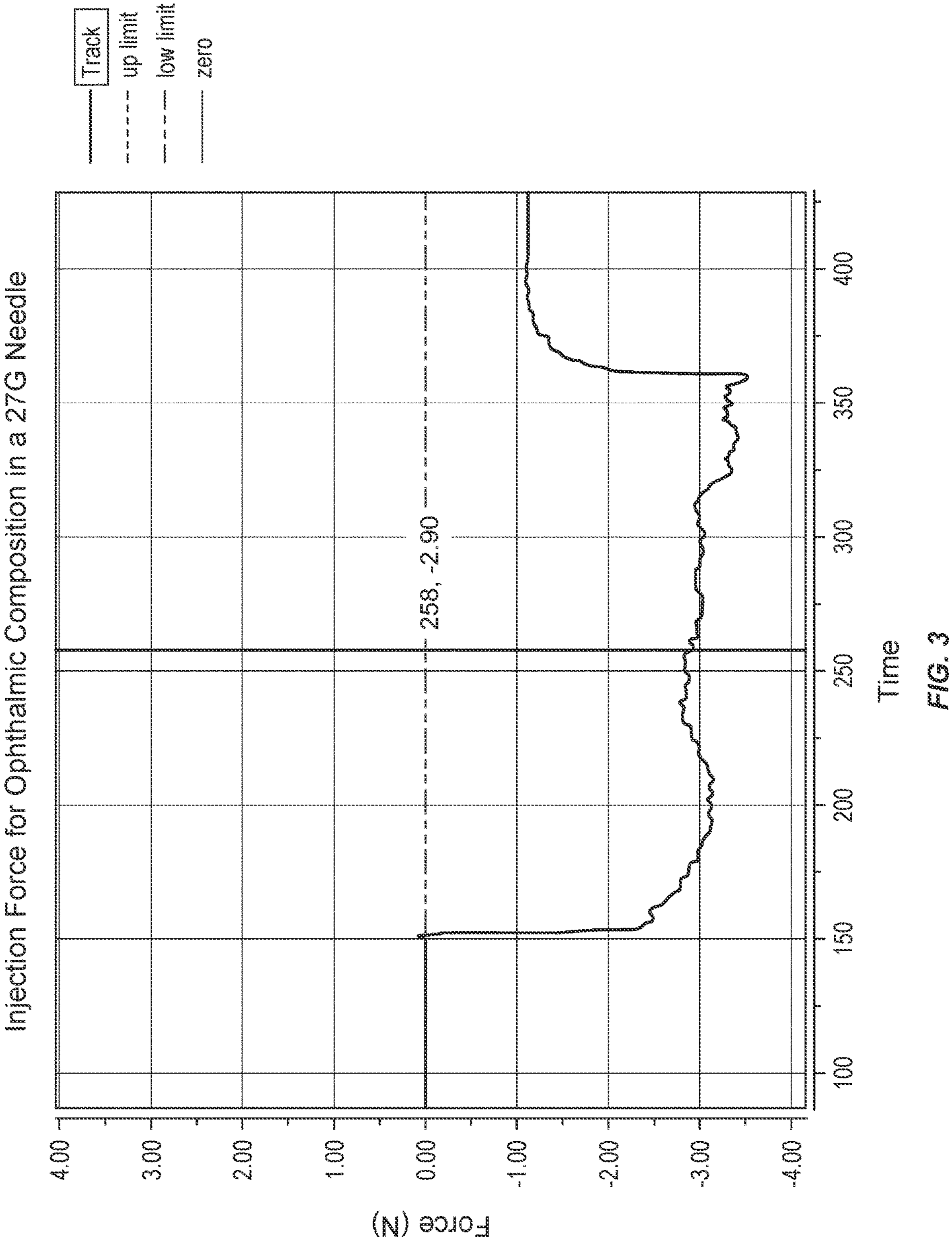
FIG. 3 is a plot of injection force with the force in N for an ophthalmic pharmaceutical composition in a 27 G needle.
Figure 4:
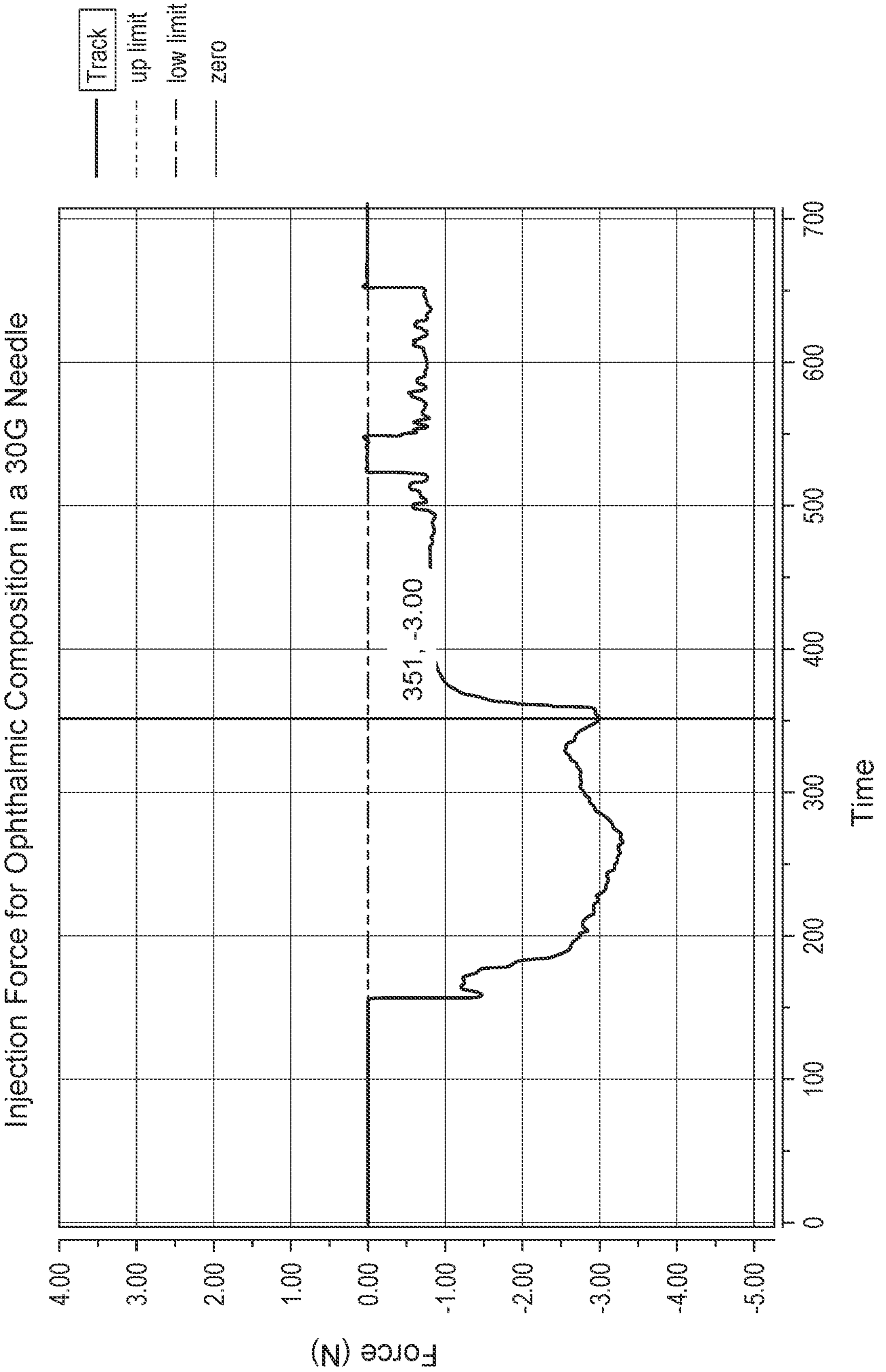
FIG. 4 is a plot of injection force with the force in N for an ophthalmic pharmaceutical composition in a 30 G needle.

The injection force plots are set forth in FIG. 3 (27 Gauge syringe needle) and FIG. 4 (30 Gauge syringe needle). The results are set forth in Table 3. The pharmaceutical composition was capable of being injected out of a 27 Gauge syringe needle and 30 Gauge syringe needle with minimal force indicating that the pharmaceutical composition is suitable for intravitreal injection.

TABLE 3

Injection Force Assessment

| Sample | Needle Diameter | Force (N) | Force (lbs) |
|---|---|---|---|
| 30 Gauge Needle | 4.54 | 3.00 | 0.674 |
| 27 Gauge Needle | 4.54 | 2.90 | 0.652 |

Example 4

The impurities in the pharmaceutical composition were assessed using HPLC chromatography. The pharmaceutical composition was assessed pre-gamma irradiation and post-gamma irradiation. The HPLC assays were conducted using the conditions set forth in Table 4.

TABLE 4

HPLC Conditions

| | | | | |
|---|---|---|---|---|
| System | HP Agilent 1100; system 25 | | | |
| Column | Accucore XL C18 150 mm × 4.6 mm, 4 μm (ThermoFisher) (LPI #678) | | | |
| Mobile phase A | DI Water | | | |
| Mobile phase B | 10 mM Ammonium Acetate buffer (6.5):Acetonitrile = 45:55 | | | |
| Gradient | Time (Minutes) | % Mobile Phase A | % Mobile Phase B | Flow Rate (mL/min) |
| | 0 | 10 | 90 | 1 |
| | 10 | 10 | 90 | 1 |
| Run Time | 10 minutes | | | |
| Autosampler Temperature | 5° C. | | | |
| Column Temperature | 30 ± .8° C. | | | |
| Detection | UV 215 nm | | | |
| Injection volume | 5 μL | | | |
| Standard Conc. | 0.08 mg/mL | | | |
| Diluent | DI Water:ACN = 1:1 | | | |

Figure 5:
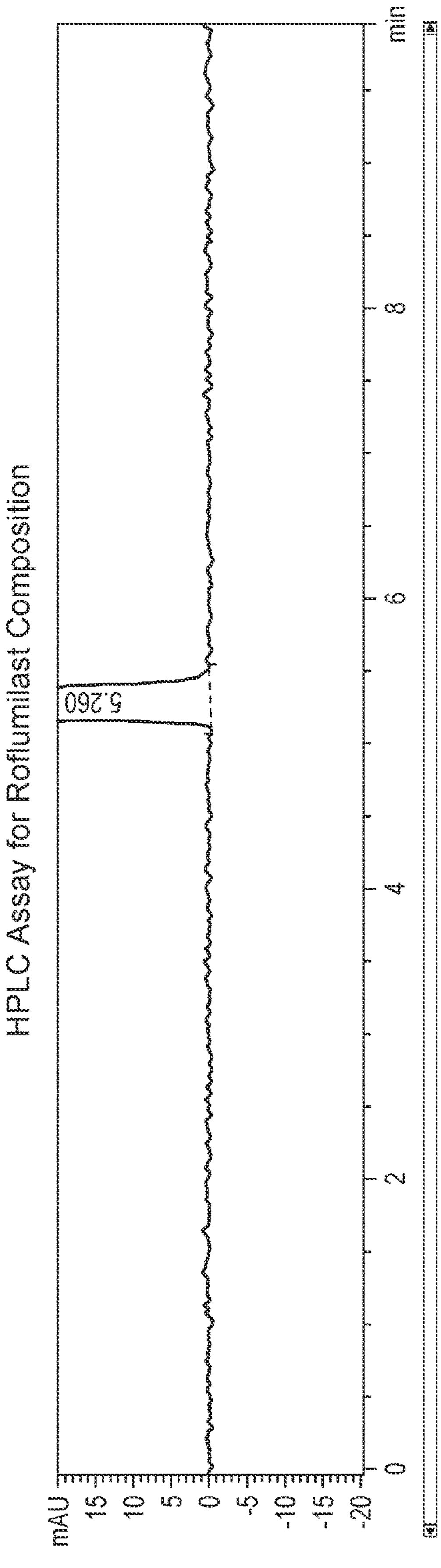
FIG. 5 is an HPLC assay for an ophthalmic pharmaceutical composition of an exemplary pharmaceutical composition.
Figure 6:
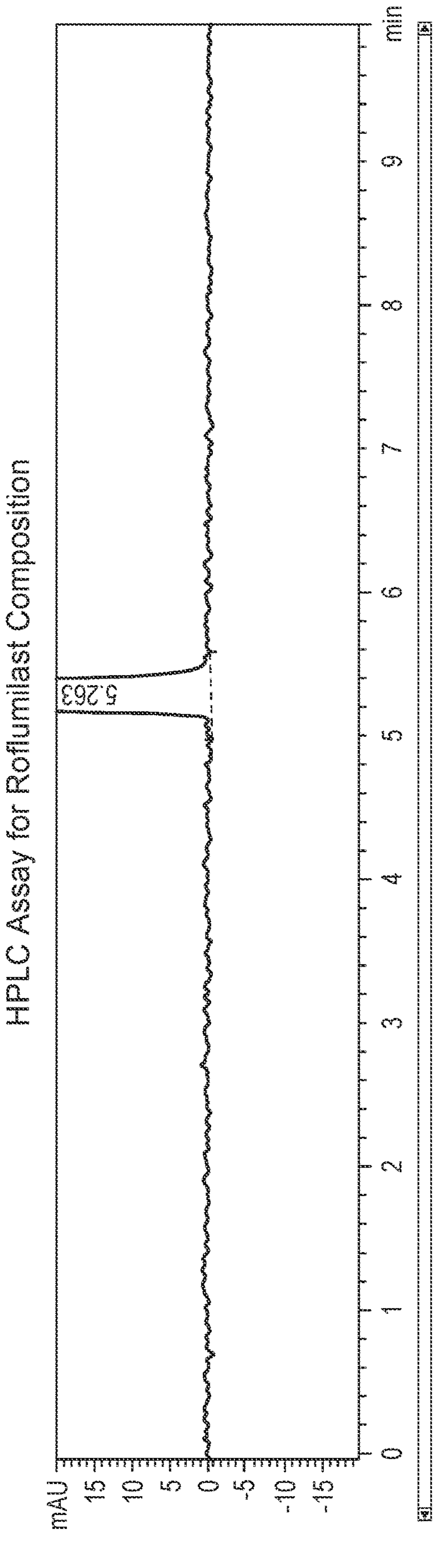
FIG. 6 is an HPLC assay for an ophthalmic pharmaceutical composition of an exemplary pharmaceutical composition.

The HPLC chromatograms are set forth in FIG. 5 (pre-gamma irradiation) and FIG. 6 (post-gamma irradiation). The HPLC chromatogram indicates that no significant, detectable (LLOQ) impurities were observed in the post-gamma irradiation samples.

Figure 7A:
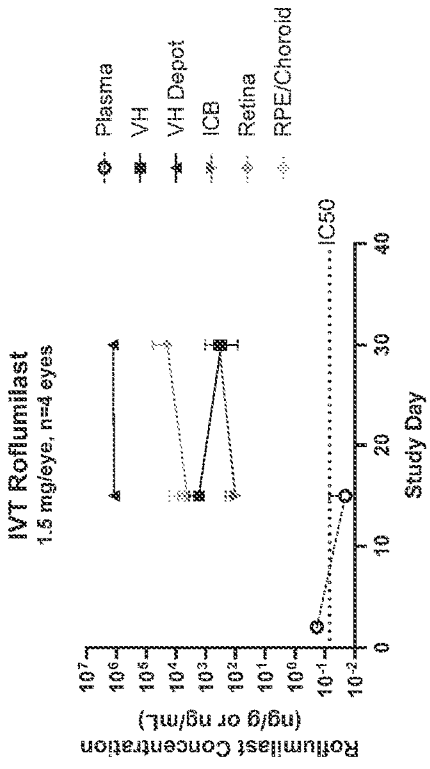
FIG. 7A-D are plots of tissue residence of roflumilast and roflumilast n-oxide at 15 days and 30 days for key retinal/posterior or vitreous tissues, after a single dose (50 uL) of 3% pharmaceutical composition via intravitreal injection, or suprachoroidal injection, into the vitreous humor and the suprachoroidal space, respectively.
Figure 7B:
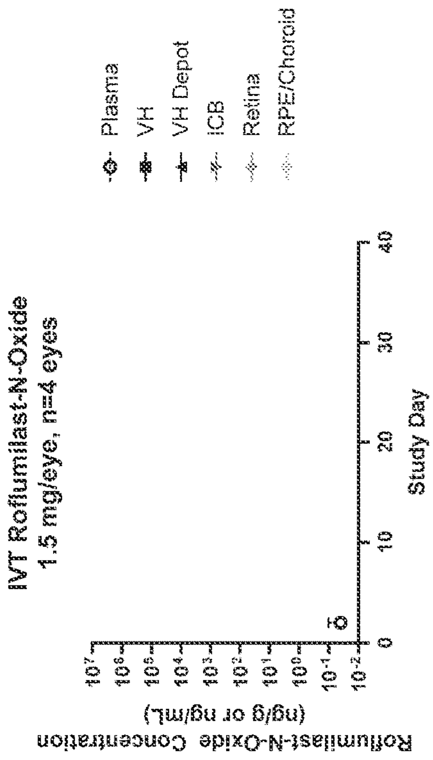
Figure 7C:
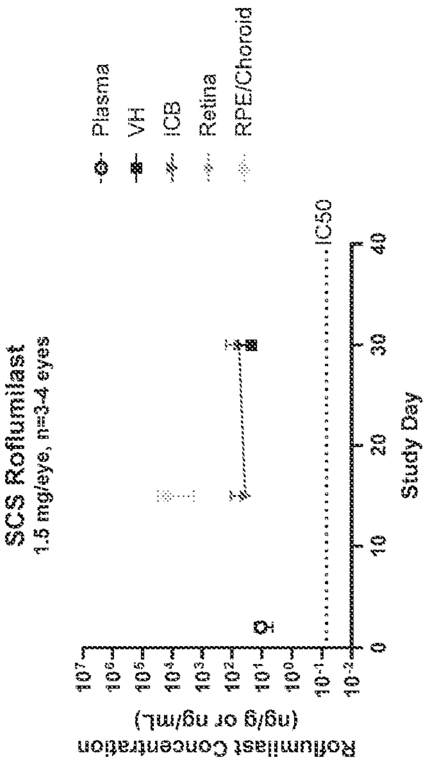
Figure 7D:
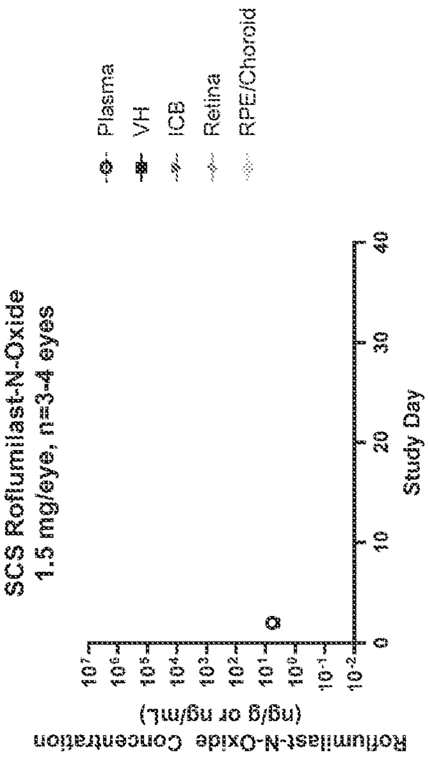

The ability to provide tissue residence at therapeutic levels was tested, and the results outlined in FIG. 7A-D. In the experiment, 10/group Dutch Belted Rabbits were given a single dose of the ophthalmic pharmaceutical composition described in Example 1 at day 1, either as a bilateral intravitreal (IVT) or suprachoroidal (SCS) injection. Ocular tissues, including aqueous humor, conjunctiva, sclera, cornea, iris/ciliary body, lens, vitreous humor, retina, and retinal pigmented epithelium (RPE)/choroid, and plasma were collected at pre-determined time points through 3 months post-dose. FIGS. 7A and 7B provide tissue residence of roflumilast and roflumilast N-oxide, respectively, following IVT injection. FIGS. 7C and 7D provide tissue residence of roflumilast and roflumilast N-oxide, respectively, following SCS injection. The tissue concentration results illustrate that following IVT injection, plasma exposure is minimal, unsolubilized and aggregated drug is still present in the vitreous at 30 days postdose, and therapeutically relevant concentrations of the pharmaceutical are present in the vitreous, iris/ciliary body, retina, and retinal pigmented epithelium (RPE)/choroid at up to 30 days postdose. Following SCS injection, plasma concentrations were higher than for IVT, and therapeutically relevant concentrations were noted in the iris/ciliary body and RPE/choroid on Day 15 and in the vitreous and iris/ciliary body on Day 30.

Figure 8:
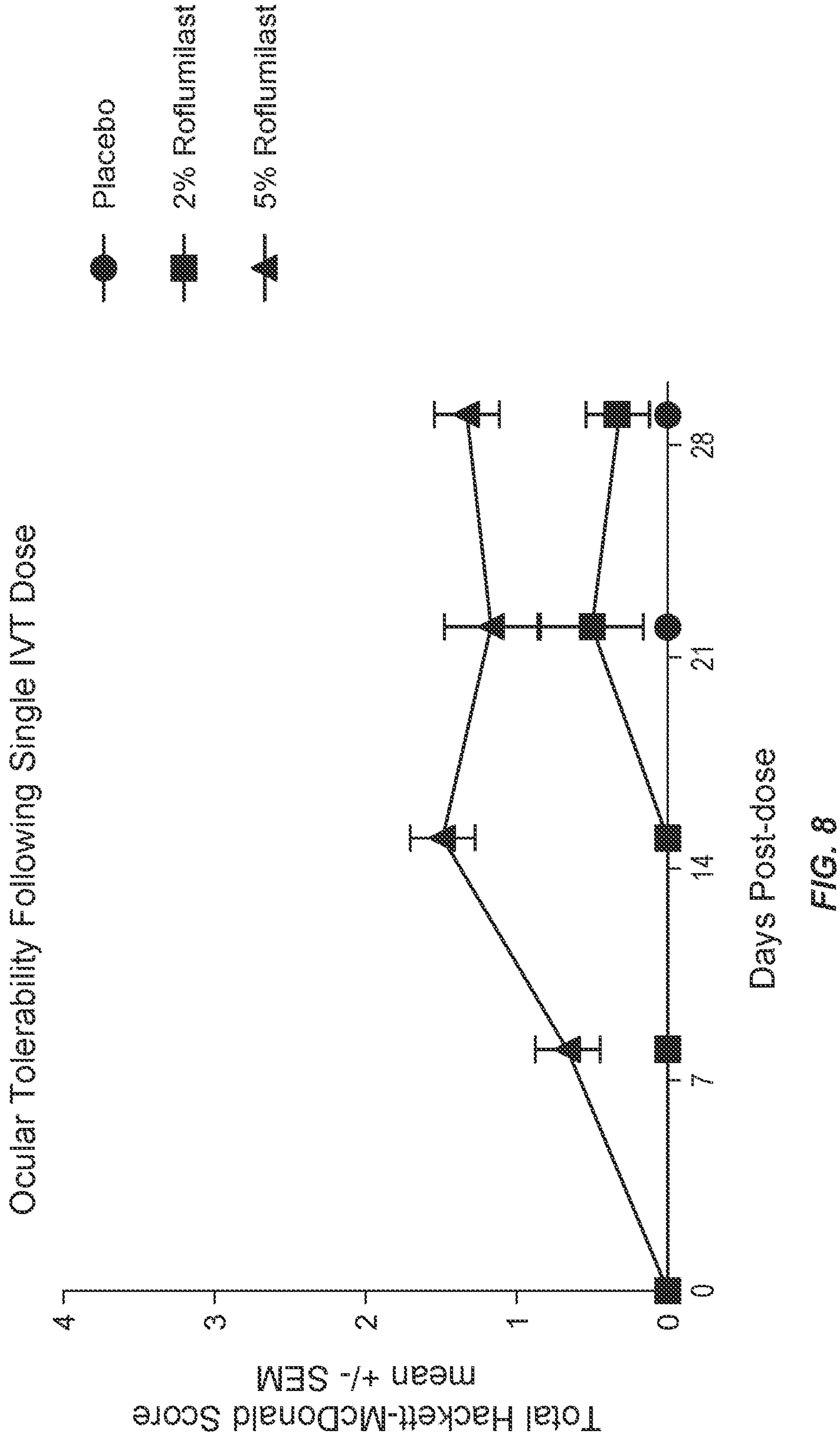
FIG. 8 is a plot of the of the ocular tolerability scores of a dose-ranging experiment including bilateral intravitreal injections of a vehicle, 2%, and 5% of ophthalmic pharmaceutical composition in Dutch Belted Rabbits, in which a self-aggregating depot of product was visible in the vitreous out to 60 days.

FIG. 8 shows the ocular tolerability scores for 3/group Dutch Belted Rabbits given a single bilateral intravitreal administration of the formulation described in Example 1, either a vehicle/0%, 2% or 5% ophthalmic pharmaceutical composition (Example 1 with modified concentration of roflumilast) and watched for 28 days. The ocular tolerability dose ranging study indicates that the product is generally tolerable, with no injection site issues, or general inflammation, with no snowglobe effect in the vitreous or aggregation on the lens. The product created a self-aggregating depot, with no particles noted throughout the vitreous, or aggregation on the lens, both of which are important for vision. The 5% composition resulted in a slightly higher incidence/severity of vitreal cells, but the 2% composition was found to be generally well tolerated.

The foregoing description has been presented for purposes of illustration and description. This description is not intended to limit the invention to the precise form disclosed. Persons of ordinary skill in the art will appreciate that modifications and substitutions of the basic inventive description may be made.

What is claimed is:

1. A high concentration ophthalmic pharmaceutical composition comprising:

about 2% to about 5% w/v of roflumilast;

a viscosity agent selected from the group consisting of hydroxypropyl methylcellulose, polyvinylpyrrolidone, or sodium carboxymethyl cellulose;

a tonicity agent comprising sodium chloride;

a surfactant;

a buffer; and water, wherein the ophthalmic pharmaceutical composition is suitable for intravitreal administration into the eye.

2. The ophthalmic pharmaceutical composition of claim 1, wherein the viscosity agent is sodium carboxymethyl cellulose.

3. The ophthalmic pharmaceutical composition of claim 1, wherein the buffer is sodium acetate and sodium citrate.

4. The ophthalmic pharmaceutical composition of claim 1, wherein the surfactant is a polysorbate.

5. The ophthalmic pharmaceutical composition of claim 1, wherein the pH of the composition is between 5.5 and 7.5.

6. The ophthalmic pharmaceutical composition of claim 1, wherein the ophthalmic pharmaceutical formulation does not include any preservatives or anti-microbial agents.

7. The ophthalmic pharmaceutical composition of claim 1, wherein the pharmaceutical composition has a particle size distribution characterized by a d90 value of less than or equal to about 15 μm.

8. The ophthalmic pharmaceutical composition of claim 1, wherein the pharmaceutical composition is capable of being injected from a 30G syringe needle with a force of less than about 3.50 N from a 30G needle.

9. The ophthalmic pharmaceutical composition of claim 1, wherein the pharmaceutical composition is capable of being injected from a 27G syringe needle with a force of less than about 3.00 N.

10. The ophthalmic pharmaceutical composition of claim 1, wherein the pharmaceutical composition has been subjected to terminal sterilization by gamma irradiation or dry heat sterilization to achieve less than about 0.2% impurities.

11. A high concentration ophthalmic pharmaceutical composition comprising:

about 2% to about 5% w/v of roflumilast;

about 0.2% to about 0.8% w/v of sodium carboxymethyl cellulose;

about 0.2% to about 0.8% w/v of sodium chloride;

about 0.02% to about 0.25% w/v of polysorbate 20;

about 0.005% to about 0.20% w/v of potassium chloride;

about 0.005% to about 0.20% w/v of calcium chloride;

about 0.005% to about 0.20% w/v of magnesium chloride;

about 0.005% to about 0.20% w/v of sodium acetate;

about 0.005% to about 0.20% w/v of sodium citrate; and water, wherein the pH of the composition is between 5.5 and 7.5, and wherein the ophthalmic pharmaceutical composition is suitable for intravitreal administration into the eye.

12. The ophthalmic pharmaceutical composition of claim 11, wherein the pharmaceutical composition has a particle size distribution characterized by a d90 value of less than or equal to about 15 μm.

13. The ophthalmic pharmaceutical composition of claim 11, wherein the pharmaceutical composition is capable of being injected from a 30G syringe needle with a force of less than about 3.50 N from a 30G needle.

14. The ophthalmic pharmaceutical composition of claim 11, wherein the pharmaceutical composition is capable of being injected from a 27G syringe needle with a force of less than about 3.00 N.

15. The ophthalmic pharmaceutical composition of claim 11, wherein the pharmaceutical composition has been subjected to terminal sterilization by gamma irradiation or dry heat sterilization to achieve less than about 0.2% impurities.

16. A method for treating an eye disorder in a patient comprising:

injecting a high concentration ophthalmic pharmaceutical composition of roflumilast into the eye of the patient, wherein the pharmaceutical composition comprises about 2% to about 5% w/v of roflumilast; a viscosity agent; a tonicity agent; a buffer agent; a surfactant; and water;

wherein the ophthalmic pharmaceutical composition is suitable for intravitreal administration.

17. The method of claim 16, wherein the eye disorder is selected from the group consisting of anterior, posterior, pan or intermediate uveitis, uveitis associated with HLA-B27, juvenile idiopathic arthritis, Behcets disease, ankylosing spondylitis, Vogt-Koyanagi-Harada disease (VKH), or autoimmune disease, ocular graft vs host disease, Stevens-Johnson syndrome/toxic epidermal necrolysis, diabetic retinopathy, diabetic macular edema, retinal vein occlusion, age-related macular degeneration (AMD) including dry, geographic atrophy, or exudative AMD, choroidal neovascularization, retinal vasculitis (drug related/iatrogenic, non-infectious/sterile, or idiopathic), choroidal thickening associated with thyroid eye disease, Coats' disease, central serous retinopathy or chorioretinopathy, sterile or infectious endopthalmitis, retinitis, choroiditis, anterior or posterior sclertis/episcleritis, endothelial keratitis (bacterial, viral, fungal, or non-infectious in nature), and other inflammatory diseases of the anterior and posterior tissues of the eye or ocular complications of other inflammatory or autoimmune diseases, inflammation associated with inherited retinal diseases, retinitis pigmentosa, Stargardt disease, Leber congenital amaurosis, Leber hereditary optic neuropathy, Usher syndrome, X-linked retinoschisis, choroidemia, zonal occult outer retinopathy, myopia, vitreomacular adhesion, retinal detachment, choroidal detachment and hemorrhage, choroidal rupture, choroidal folds, proliferative vitreoretinopathy, idiopathic ischemia, achromatopsia, retinopathy of prematurity, gyrate atrophy, central areolar choroidal dystrophy, punctate inner choroidopathy, multifocal choroiditis, choroiditis, choroidal granuloma, choroidal dystrophy, choroidal fibrosis, acute posterior multifocal placoid pigment epitheliopathy, serpiginous choroidopathy, birdshot retinochoroidopathy, multiple evanescent white dot syndrome, retinoblastoma, choroidal melanoma, retinal lymphoma, iatrogenic posterior and vitreous chamber inflammation.

18. The method of claim 16, wherein the pharmaceutical composition results in a well tolerated delivery and use.

19. The method of claim 17, wherein the pharmaceutical composition delivers a therapeutic level of roflumilast to one or more of the cornea, limbus, conjunctiva, eyelids, lacrimal and Meibomian glands, lens, pupil, iris, anterior sclera, ciliary body, lacrimal glands, aqueous humor, the internal or endothelial or inner layer of the cornea, lacrimal glands, lymph nodes, posterior sclera, retina, choroid, macula, fovea, optic disc, optic nerve, vitreous humor, hyaloid canal, or extraorbital or periorbital tissues and muscle/connective tissues.

* * * * *